United States Patent [19]

Batina et al.

[11] Patent Number: 4,550,731
[45] Date of Patent: Nov. 5, 1985

[54] ACQUISITION CIRCUIT FOR CARDIAC PACER

[75] Inventors: William P. Batina; Robert M. White, both of Miami, Fla.

[73] Assignee: Cordis Corporation, Miami, Fla.

[21] Appl. No.: 587,262

[22] Filed: Mar. 7, 1984

[51] Int. Cl.⁴ .............................................. A61N 1/36
[52] U.S. Cl. ............................ 128/419 PT; 128/697; 128/903
[58] Field of Search ............... 128/419 PG, 419 PS, 128/419 PT, 697, 903

[56] References Cited

U.S. PATENT DOCUMENTS

| | | | |
|---|---|---|---|
| 3,942,535 | 3/1976 | Schulman | 128/419 PS |
| 4,082,097 | 4/1978 | Mann et al. | 128/419 PS |
| 4,324,251 | 4/1982 | Mann | 128/419 PT |
| 4,361,153 | 11/1982 | Slocum et al. | 128/419 PT |

Primary Examiner—William E. Kamm
Attorney, Agent, or Firm—George H. Gerstman

[57] ABSTRACT

An acquisition circuit for a cardiac pacer includes an oscillator for producing an externally generated magnetic signal at a first predetermined frequency. An implantable cardiac pacer has a tuned inductor coil to be responsive to the magnetic signal for developing an induced signal with a phase-shift. Light-emitting devices are responsive to the magnetic signal and the induced signal are provided for transmitting optical signals which change gradually from flashing to a steady on condition when the telemetry head is moved closer to and adequately positioned over the cardiac pacer to indicate that positive acquisition has been obtained.

16 Claims, 5 Drawing Figures

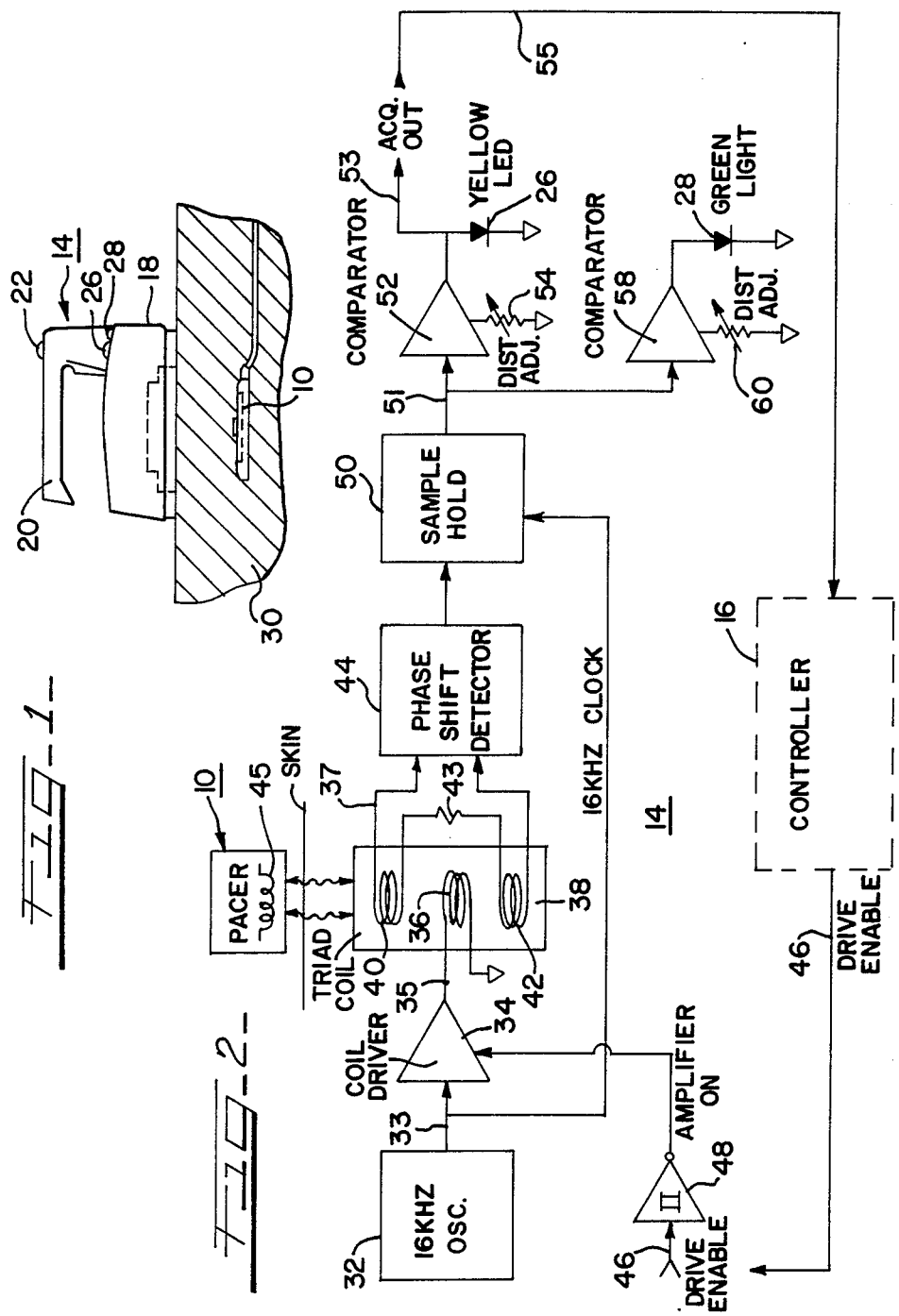

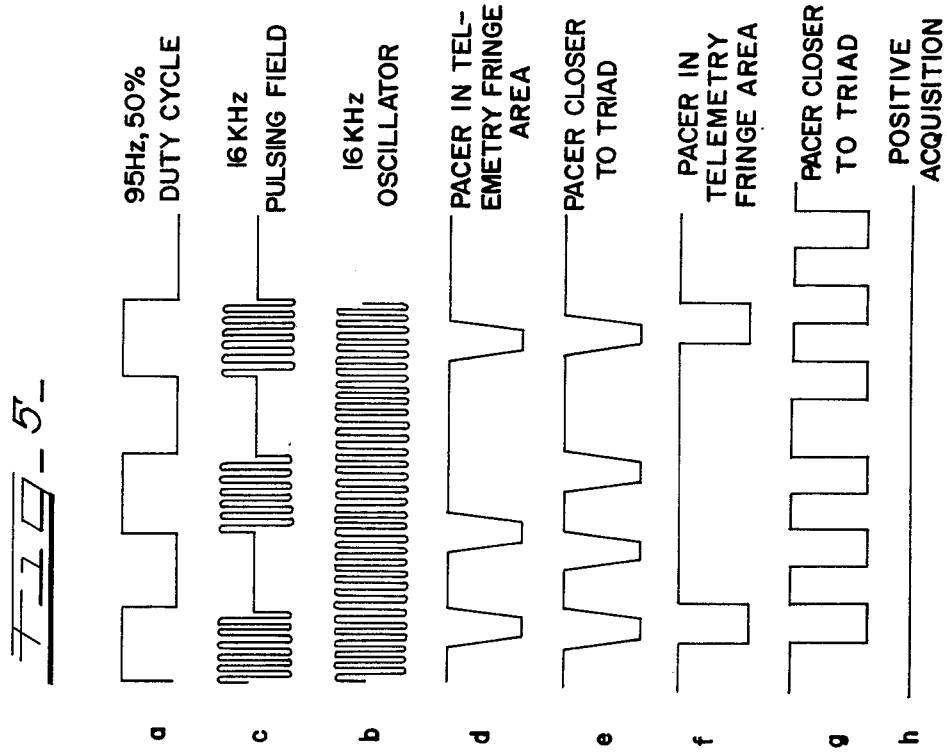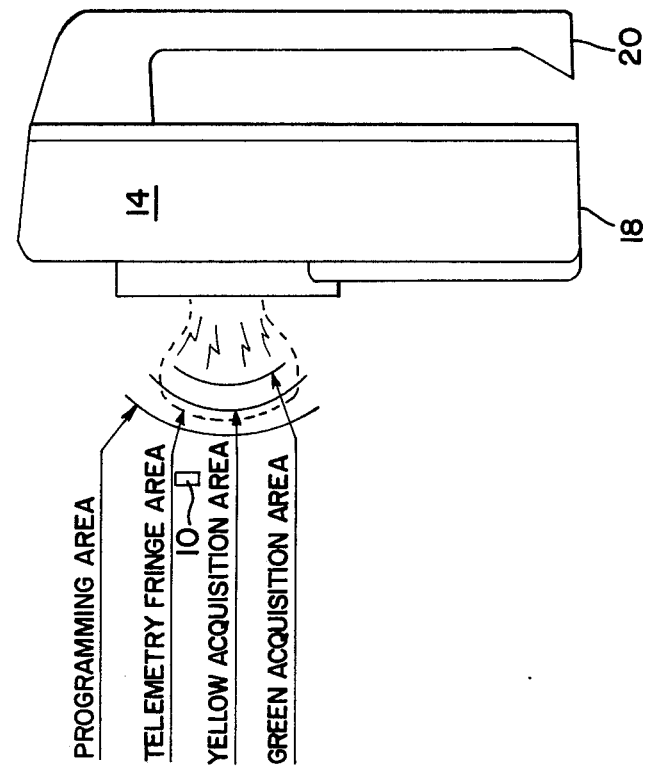

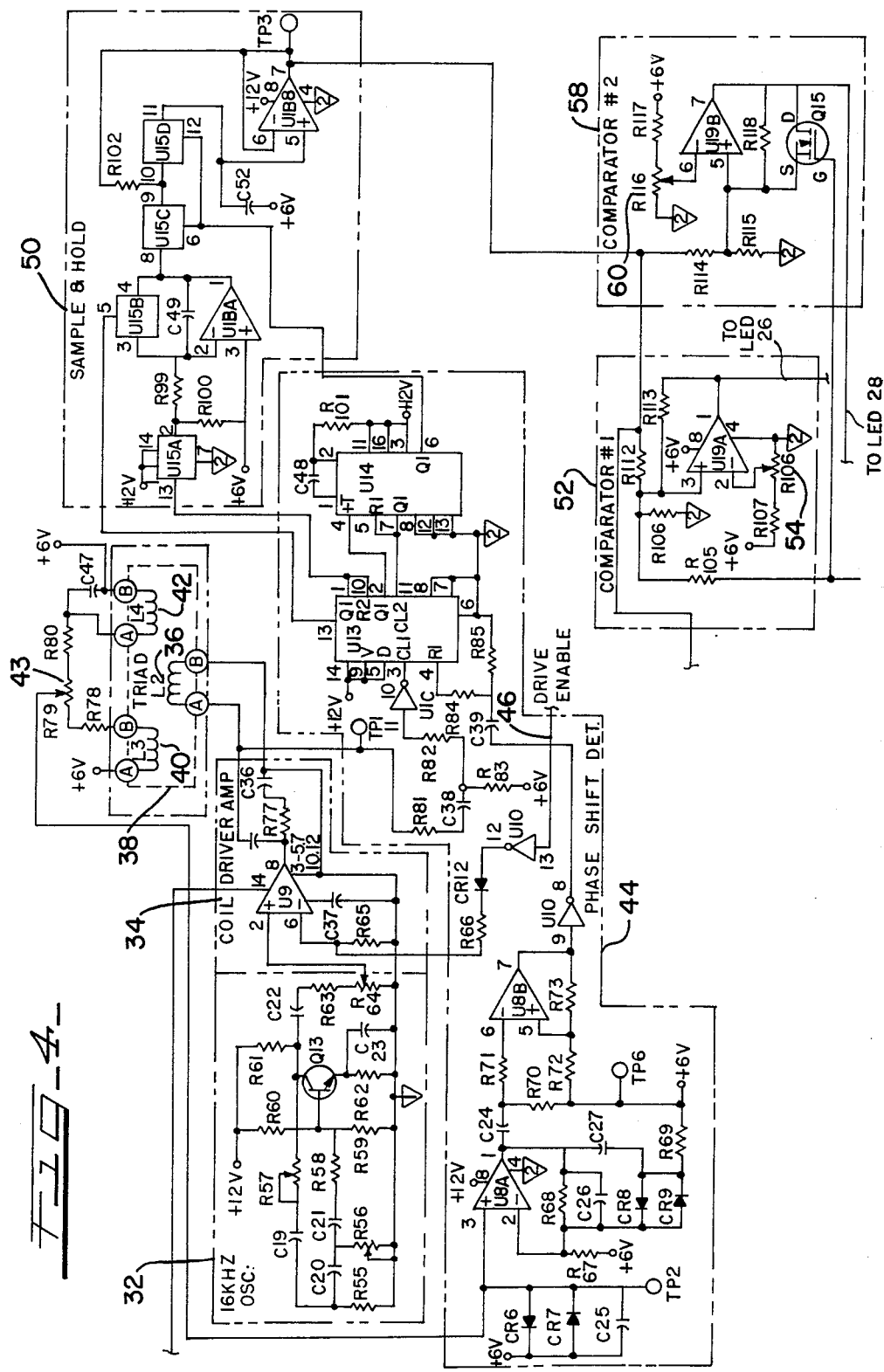

ACQUISITION CIRCUIT FOR CARDIAC PACER

BACKGROUND OF THE INVENTION

This invention relates generally to electronic implants or cardiac pacers and more particularly, it relates to an acquisition circuit for use in conjunction with a cardiac pacer of an implanted telemetry system.

In U.S. Pat. No. 4,361,153, Slocum, et. al., entitled "Implant Telemetry System" and assigned to the same assignee of the present invention, there is disclosed a hand-held two-way external telemetry head and a physiological stimulator, "a cardiac pacer", implanted in suitable portion of a human body. When a physician desires to change the programmed to pulse parameters so as to prescribe a different stimulation therapy program for the patient, he positions the telemetry head over the pacer or "implant" to carry on two-way communication. In order to indicate to the physician that the telemetry head is adequately positioned with respect to the "implant" before data is transmitted therefrom, the output level of an external phase comparator in the telemetry head must exceed a given threshold level to turn on a light emitting device for signifying "acquistion".

Since proper location of the telemetry head with respect to the cardiac pacer is so critical in programming telemetry pacers, it would therefore be desirable to provide an acquisition circuit which gives the physician enhanced confidence when a positive acquisition has been obtained. To this end, the present invention provides an acquisition circuit where the light-emitting diodes change gradually from flashing to a solid on condition to indicate a positive acquisition.

SUMMARY OF THE INVENTION

Accordingly, it is a general object of the present invention to provide an acquisition circuit in a telemetry head to indicate more reliably that the telemetry head is adequately positioned over the "implant" to signify positive acquisition.

It is still another object of the present invention to provide an acquisition circuit having indicating means for transmitting optical signals which change gradually from flashing to a steady on condition when the telemetry head is moved closer to and adequately positioned over the implant.

It is still yet another object of the present invention to provide an acquisition circuit wherein light-emitting diodes change gradually from flashing to a solid on condition to indicate a positive acquisition.

In accordance with the aim and objectives of the present invention, there is provided an acquisition circuit for a cardiac pacer to indicate when an external telemetry head is adequately positioned over an electronic stimulator implanted in a human body for data transmission. The acquisition circuit includes oscillator means for producing an externally generated magnetic signal at a first predetermined frequency. Enabling means is provided for generating a second signal at a second predetermined frequency which is lower than the first signal. Drive means is provided for combining the magnetic signal and the second signal to produce a third signal containing the second signal enveloped within the magnetic signal for each half cycle. An implantable pacer includes an inductor means tuned to the first frequency for generating an induced signal in the presence of the magnetic signal at the same frequency to which the inductor means is tuned. The induced signal has a phase shift relative to the magnetic signal dependent upon the distance of the pacer to the telemetry head. Circuit means responsive to the third signal and the induced signal is provided for generating pulses proportioned to the amount of phase shift. Indicating means coupled to the circuit means is provided for transmitting optical signals which change gradually from flashing to a steady on as the pulse signals from the circuit means increase when the telemetry head is moved closer to and adequately positioned over the implant to indicate that positive acquisition has been obtained.

BRIEF DESCRIPTION OF THE DRAWINGS

These and other objects and advantages of the present invention will become more fully apparent from the following detailed description when read in conjunction with the accompanying drawings with like reference numerals indicating corresponding like parts throughout, wherein:

FIG. 1 is a schematic representation of the use of the telemetry system consisting of a programming/telemetry head and an implant, according to the present invention;

FIG. 2 is a block diagram of the telemetry system with the acquisition circuit in the telemetry head of FIG. 1;

FIG. 3 is a more detailed view of the telemetry head of FIG. 1;

FIG. 4 is a schematic circuit diagram showing circuitry suitable for use in certain of the blocks shown in FIG. 2; and FIG. 5 is a timing diagram of signals associated with the acquisition circuit of FIG. 2.

DESCRIPTION OF THE PREFERRED EMBODIMENT

Referring now in detail to the various views of the drawings, there is shown in FIG. 1 a schematic representation of the overall telemetry system which includes an electronic implant or cardiac pacer 10 of the type manufactured by Cordis Corporation for communicating with a positionable external hand-held programming/telemetry head 14. As can be seen from FIG. 2, the head 14 has a microprocessor-based controller 16 for establishing and programming certain parameters in accordance with transmitted data received from the pacer 10. The head 14 includes a body member 18 and an integral handle portion 20 with pushbutton 22. Yellow and green light-emitting diodes (LED) 26 and 28 are mounted on the upper surface of the body member 18 to indicate where there is a positive acquisition, as will be more fully described later. The cardiac pacer 10 is implanted with electrical leads connected in a suitable portion of a human body 30. A user such as a physician places the face of the telemetry head 14 against the patient's skin adjacent to the pacer 10 for noninvasive two-way communication with the pacer.

FIG. 2 illustrates in block diagram form the telemetry system with the acquisition circuit in telemetry head 14 of the present invention. The acquisition circuit, which senses the proximity of the telemetry head 14 to the implant 10, includes an oscillator 32 which produces a continuing myriametric frequency electrical output at approximately 16 kHz. The output of the oscillator 32 is fed via coil driver amplifier 34 to a middle coil 36 triple coil assembly or triad coil 38. The corresponding ends of outer coils 40 and 42 are interconnected by a potentiometer 43 and each of the other ends of the coils 40 and 42 are fed as inputs to phase shift detector 44.

In the implant 10, a tuned coil 45 is centered at the frequency of 16 kHz. The oscillating current through the pick-up coil 40 in the telemetry head 14 establishes a magnetic field which radiates into the adjacent implant and induces a corresponding voltage in the tuned coil 45 which, in turn, re-radiates a second magnetic field at the same frequency but with a phase shift. The amount of phase shift in the reflected or induced signal is dependent upon the distance and/or position of the telemetry head to the implant.

For tuning on the acquisition circuit, a pulsating Drive Enable electrical signal at a frequency of 95 Hz with a 50 percent duty cycle is received on line 46 which is generated by the microprocessor-controller 16 in the head 14. This DRIVE ENABLE signal is delivered by an inverter 48 to a second input of the coil drive amplifier 34. The output of the phase shift detector 44 is fed to one input of a sample and hold circuit 50. The other input of the sample and hold circuit is fed from the output of the oscillator 32.

The output of the sample and hold circuit 50 as applied to a first comparator 52 with an adjustable threshold controlled by a potentiometer 54 for driving a yellow LED 26. Further, the output of the sample and hold circuit 50 is also applied to a second comparator 58 with an adjustable threshold controlled by a potentiometer 60 for driving a green LED 28.

For completeness in the disclosure of the above-described system, but not for purposes of limitation, the following representative values and component identifications of the circuits shown in FIG. 4 are submitted. These values and components who are employed in a system that was constructed and tested and which provides high quality performance. Those skilled in the art will recognize that many alternative elements and values may be employed in constructing systems and circuits in accordance with the present invention.

| Part | Value or Component |
|---|---|
| Oscillator 32 | |
| R55 | 8.2 Kilohms |
| R56 | 20 Kilohms pot |
| R57 | 50 Kilohms pot |
| R58 | 6.8 Kilohms |
| R59, R61 | 10 Kilohms |
| R60 | 68 Kilohms |
| R62 | 3.3 Kilohms |
| R63 | 43 Kilohms |
| R64 | 5 Kilohms |
| C19, C20, C21 | 470 Picofarads |
| C22 | 680 Picofarads |
| C23 | .1 Microfarads |
| Q13 | 2N930 Transistor |
| Coil Driver Amplifer 34 | |
| R65 | 1 Kilohm |
| R77 | 2.7 Ohms |
| C35 | .22 Farad |
| C36 | .1 Microfarad |
| C37 | .68 Microfarad |
| U9 | ULN2280 Amplifier |
| Phase Shift Detector 44 | |
| R67, R85 | 5.1 Kilohms |
| R68 | 1 Megaohm |
| R69, R81, R101 | 10 Kilohms |
| R70, R71, R72 | 1 Kilohm |
| R73 | 100 Kilohms |
| R82, R84 | 2 Kilohms |
| R83 | 6.8 Kilohms |
| C25 | .001 Microfarad |
| C26 | 470 Picofarads |
| C24, C27, C38 | .01 Microfarad |
| C39 | 560 Picofarads |
| C48 | 100 Picofarads |
| CR6, CR7, CR8, CR9 | IN914 Diode |
| U8A, U8B | CA3240AE |
| U10 | CD40106B |
| U13 | 4013B |
| U14 | 4098B |
| Sample and Hold 50 | |
| R99 | 511 Kilohms |
| R100 | 10 Kilohms |
| R102 | 100 Kilohms |
| U15A-D | 4016B |
| U18A, U18B | CA3240AE |
| C52 | .002 Microfarad |
| Comparators 52, 58 | |
| R105 | 10 Kilohms |
| R106, R115 | 1 Kilohm |
| R107, R112, R114, R117 | 15 Kilohms |
| R108, R116 | 1 Kilohm pot |
| R113, R118 | 10 Megaohms |
| Q15 | ZYN0106A |
| U19A, U19B | CA3240AE |

While the two-way communication between the telemetry heads 14 and the implant 10 involves the three modes of operation: an acquisition mode, a transmission or programming mode for transmitting data to the implant and a reflected signal telemetry mode, the present invention is only concerned with the acquisition mode to insure adequate and accurate positioning of the telemetry head over the implant as shown in FIG. 1. The operation of the programming and reflected signal telemetry modes are described and illustrated in U.S. Pat. No. 4,361,153 and is hereby incorporated by reference.

Since proper location is so very critical in programming telemetry pacers, the acquisition circuit of the present invention is used to force the user to center the pacer within the programming and/or telemetry fringe or field areas which are shown in FIG. 3. In order to accomplish this positive acquisition, both of the yellow and green LEDs 26 and 28 are caused to flash off and on when the pacer enters the programming and/or telemetry fringe areas of the telemetry head. This flashing is used to alert the user that the telemetry head 14 could be better positioned. As the pacer 10 enters the yellow acquisition area, as illustrated in FIG. 3, where the pacer is about 1½ inches or less in distance from the telemetry head, the yellow LED 26 stops flashing and turns solid on and glows constantly. As the telemetry head is moved closer so that the pacer enters the green acquisition area of FIG. 3 where the pacer is about one inch or less in distance from the telemetry head, the green LED 28 also stops flashing and turns solidly on and glows constantly. Thus, the positive acquisition is defined as the point where both the yellow and green LEDs 26 and 28 are turned on solid.

Referring now to FIGS. 2, 4 and 5, in order to initiate the acquisition mode, the pushbutton 22 on the telemetry head 14 is depressed causing a pulsating DRIVE ENABLE signal on the line 46 with a frequency of 95 Hz and 50 percent duty cycle shown in FIG. 5a to be sent from the microprocessor-base controller 16 to the coil drive amplifier 34 turning it on. The output 33 of the oscillator 32 with frequency of 16 kHz is illustrated in FIG. 5b. The output signal on line 35 from the driver amplifier 34, which is the triad coil input, is depicted in FIG. 5c. A combined signal on line 37 from the output of the triad consists of a 95 Hz square wave enveloping a pulsating 16 kHz field for each half cycle. As the pacer enters the telemetry fringe area, random pulses of this combined signal ripple through the phase shift detector 44 and the sample and hold circuit 50 to yield pulse signals on line 51 as shown in FIG. 5d, thereby causing the yellow and green output LEDs to flash.

As pacer 10 enters the yellow acquisition area and then further enters the green acquisition area of the telemetry head, more phase shift is detected and thus more pulse signals ripple through to the output of circuit 50 as shown in FIG. 5e. This causes the LEDs 26 and 28 to flash at a faster rate and eventually turn on solid. The outputs of the acquisition circuit from the first comparator 52 on line 53 are shown in FIGS. 5f and 5g corresponding to when the inputs to the comparator 52 are as illustrated in FIGS. 5d and 5g, respectively. The output on line 55 of the acquisition circuit is shown in FIG. 5h when positive acquisition has been obtained so as both the yellow and green LEDs are turned on solid. As a result, the user sees a gradual change in the yellow and green output LEDs from flashing to solid on as the telemetry head 14 nears the implant 10. Further, the intensity of the LEDs will change from dim to bright on positive acquisition.

From the foregoing detailed description, it can thus be seen that the present invention provides an acquisition circuit for a cardiac pacer to indicate when an external telemetry head is adequately positioned over an electronic stimulator implanted in a human body for data transmission. The acquisition circuit includes indicating means for transmitting optical signals which change from flashing to a steady on condition as the telemetry head is moved closer to and adequately positioned over the implant.

While that has been illustrated and described what is at present to be a preferred embodiment of the present invention, it will be understood by those skilled in the art that various changes and modifications may be made, and equivalents may be substituted for elements thereof without departing from the central scope thereof. In addition, many modifications may be made to adapt a particular situation or material to the teachings of the present invention without departing from the central scope thereof. Therefore, it is intended that this invention not be limited to the particular embodiments disclosed as the best mode contemplated for carrying out this invention, but the invention will include all embodiments falling within the scope of the appended claims.

What is claimed is:

1. A cardiac pacing system including an acquisition circuit for a cardiac pacer to indicate when an external telemetry head is adequately positioned over an electronic stimulator implanted in a human body for data transmission comprising:

oscillator means for producing an externally generated magnetic signal at a first predetermined frequency;

enabling means for generating a second signal at a second predetermined frequency which is lower than said magnetic signal;

drive means for combining said magnetic and second signals to provide a third signal containing said second signal enveloping said magnetic signal for each half cycle;

an implantable pacer including an inductor coil means tuned to said magnetic signal frequency for generating an induced signal in the presence of said magnetic signal at the same frequency to which said coil means in tuned, means for providing, to said induced signal, a phase-shift relative to said magnetic signal dependent upon the distance of said pacer to said telemetry head;

circuit means responsive to said magnetic signal and said induced signal for generating pulse signals when said telemetry head is over said electronic stimulator; and indicating means coupled to said circuit means for transmitting signals changing from pulsing to a steady on condition as the pulses from said circuit means increase when said telemetry head is moved closer to and adequately positioned over said implant to indicate that positive acquisition has been obtained.

2. A cardiac pacing system as claimed in claim 1, wherein said magnetic frequency of said oscillator means is approximately 16 kHz.

3. A cardiac pacing system as claimed in claim 1, wherein said second frequency of said enabling means is approximately 95 Hz.

4. A cardiac pacing system as claimed in claim 1, wherein said drive means comprises a coil driver amplifier.

5. A cardiac pacing system as claimed in claim 1, wherein said circuit means includes a phase-shift detector and a sample and hold circuit.

6. A cardiac pacing system as claimed in claim 1, wherein said indicating means comprises a first comparator means and a first light-emitting diode coupled to the output of said first comparator means, and a second comparator means and a second light-emitting diode coupled to the output of second comparator means;

means for biasing said first comparator means to control energization of said first light-emitting diode in response to detection of a first detected amount of phase shift and means for biasing said second comparator means to control energization of said second light-emitting diode in response to detection of an additional amount of detected phase shift; and means connecting said circuit means to said first and second comparator means.

7. A cardiac pacing system as claimed in claim 6, wherein said first light-emitting diode is yellow and said second light-emitting diode is green.

8. A cardiac pacing system as claimed in claim 6, wherein said first and second light-emitting diodes change gradually from flashing to a steady on condition when said telemetry head is moved closer to and adequately positioned over said implant.

9. A cardiac pacing system including an acquisition circuit for a cardiac pacer to indicate when an external telemetry head is adequately positioned over an electronic stimulator implanted in a human body for data transmission comprising:

a telemetry head including acquisition circuit means for indicating when said telemetry head is adequately positioned over an implanted cardiac pacer;

said acquisition circuit means including oscillator means for producing an externally generated magnetic signal at a first predetermined frequency;

enabling means for generating a second signal at a second predetermined frequency which is lower than said magnetic frequency;

an implantable cardiac pacer including inductor means to be responsive to said magnetic signal for developing an induced signal with a phase shift; and said acquisition circuit further includes indicating means for transmitting optical signals changing from flashing to a steady on condition when said telemetry head is moved closer to and is adequately positioned over said cardiac pacer to indicate that positive acquisition has been obtained, said indicating means providing a flashing rate in inverse proportion to the proximity of the telemetry head to said cardiac pacer.

10. A cardiac pacing system as claimed in claim 9, wherein said magnetic frequency of said oscillator means is approximately 16 kHz.

11. A cardiac pacing system as claimed in claim 10, further comprising means for combining said magnetic and second signals to provide a third signal containing said second signal enveloping said magnetic signal for each half cycle.

12. A cardiac pacing system as claimed in claim 11, further comprising a phase-shift detector and a sample and hold circuit which is responsive to said magnetic signal and said induced signal for generating pulse signals when said telemetry head is over said pacer.

13. A cardiac pacing system as claimed in claim 9, wherein said indicating means comprises a first comparator means and a first light-emitting diode coupled to the output of said first comparator means, and a second comparator means and a second light-emitting diode coupled to the output of second comparator means;

means for biasing said first comparator means to control energization of said first light-emitting diode in response to detection of a first detected amount of phase shift and means for biasing said second comparator means to control energization of said second light-emitting diode in response to detection of an additional amount of detected phase shift; and means connecting said circuit means to said first and second comparator means.

14. A cardiac pacing system as claimed in claim 13, wherein said first light-emitting diode is yellow and said second light-emitting diode is green.

15. A cardiac pacing system as claimed in claim 13, wherein said first and second light-emitting diodes change gradually from flashing to a steady on condition when said telemetry head is moved closer to and adequately positioned over said pacer.

16. A cardiac pacing system including an acquisition circuit for use in an implantable telemetry system comprising:

an external telemetry head including oscillator means for producing an externally generated magnetic signal at a predetermined frequency;

an implanted cardiac pacer including inductor means responsive to said magnetic signal for developing a re-radiated signal with a phase shift relative to said magnetic signal dependent upon the distance of said pacer to said telemetry head; and said telemetry head further including indicating means responsive to said magnetic signal and said re-radiated signal for transmitting optical signals changing from flashing to a steady on condition when said telemetry head is moved closer to and adequately positioned over said cardiac pacer to indicate that positive acquisition has been obtained, said indicating means providing a flashing rate in inverse proportion to the proximity of the telemetry head to said cardiac pacer.

* * * * *